US007064241B2

(12) United States Patent
Brown et al.

(10) Patent No.: US 7,064,241 B2
(45) Date of Patent: Jun. 20, 2006

(54) CHEMICAL AND BIOLOGICAL WARFARE DECONTAMINATING SOLUTION USING PERACIDS AND GERMINANTS IN MICROEMULSIONS, PROCESS AND PRODUCT THEREOF

(75) Inventors: Jerry S. Brown, Woodford, VA (US); Richard C. Hodge, King George, VA (US); Margaret A. McCabe, Fredericksburg, VA (US); Karen A. McGrady, Fredericksburg, VA (US); Amanda S. Schilling, Fredericksburg, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 121 days.

(21) Appl. No.: 10/664,003

(22) Filed: Sep. 16, 2003

(65) Prior Publication Data

Related U.S. Application Data

(60) Continuation-in-part of application No. 10/057,471, filed on Feb. 1, 2002, which is a division of application No. 09/477,941, filed on Jan. 5, 2000, now Pat. No. 6,369,288.

(51) Int. Cl.

| | |
|---|---|
| ***A62D 3/00*** | (2006.01) |
| ***A61L 2/18*** | (2006.01) |
| ***C11D 9/42*** | (2006.01) |

(52) U.S. Cl. ........................ 588/320; 588/401; 422/28; 422/29; 422/30; 422/32; 252/186.26; 252/186.42; 510/310; 510/375; 510/500; 510/503

(58) Field of Classification Search ................ 588/200; 422/28, 29, 30, 32; 252/186.26, 186.42; 510/310, 375, 500, 503
See application file for complete search history.

(56) References Cited

U.S. PATENT DOCUMENTS

| | | | | |
|---|---|---|---|---|
| 3,687,815 | A * | 8/1972 | Scharpf, Jr. | 435/252.5 |
| 3,956,159 | A | 5/1976 | Jones | 252/104 |
| 5,296,239 | A | 3/1994 | Colery et al. | 424/613 |
| 5,462,692 | A | 10/1995 | Roesler et al. | 252/186.26 |
| 5,516,486 | A | 5/1996 | Wright et al. | 422/28 |
| 5,612,300 | A | 3/1997 | von Blucher et al. | 510/110 |
| 5,759,989 | A | 6/1998 | Scialla et al. | 510/500 |
| 6,086,785 | A | 7/2000 | Roesler et al. | 252/186.26 |
| 6,369,288 | B1 | 4/2002 | Brown | 588/200 |
| 6,599,715 | B1 * | 7/2003 | Vanderberg et al. | 435/34 |
| 6,656,919 | B1 * | 12/2003 | Baugh et al. | 514/46 |
| 2003/0045767 | A1 | 3/2003 | Brown | 588/200 |
| 2004/0033269 | A1 * | 2/2004 | Hei et al. | 424/616 |

* cited by examiner

*Primary Examiner*—Joseph D. Anthony
(74) *Attorney, Agent, or Firm*—Gerhard W. Thielman, ESQ; Scott R. Boalick, ESQ; Matthew J. Bussan, ESQ

(57) ABSTRACT

A microemulsion composition having a solid source of peroxycarboxylic acid and germinant is used for chemical and biological warfare decontamination. A process for decontaminating uses the microemulsion composition.

11 Claims, No Drawings

CHEMICAL AND BIOLOGICAL WARFARE DECONTAMINATING SOLUTION USING PERACIDS AND GERMINANTS IN MICROEMULSIONS, PROCESS AND PRODUCT THEREOF

This application is a continuation-in-part of U.S. patent application Ser. No. 10/057,471 filed on Feb. 1, 2002, entitled "Chemical and Biological Warfare Decontaminating Solution Using Bleach Activators", which is a divisional of U.S. patent application Ser. No. 09/477,941 filed on Jan. 5, 2000, now U.S. Pat. No. 6,369,288, issued Apr. 9, 2002, entitled "Chemical and Biological Warfare Decontaminating Solution Using Bleach Activators".

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention provides a chemical warfare agent decontamination (decon) solution. More particularly, the decontamination solution includes a microemulsion composition having a solid source of peroxycarboxylic acid dissolved in the microemulsion and a germinant in combination with the solid peroxycarboxylic acid. The decontaminating solution is useful in neutralizing chemical and biological warfare agents.

2. Brief Description of the Related Art

Chemical agents (CA) and biological agents (BA), (collectively CB agents) are becoming an increasingly problematic to military commander and civil authorities. Use of these agents is known in chemical (CW) and biological (BW) warfare. Biological agents are particulates that include microorganisms such as bacteria, viruses and fungi. Unlike chemical agents, a time delay may occur before the full extent of the effects of the biological agents become apparent. In some biological agents, such as anthrax, spore production enables biological agents to remain in an environment for years while retaining biological activity.

Chemical agents, used as CW agents, include vesicants such as Sulfur Mustard (HD), Nitrogen Mustard (HN-1; HN-2 and HN-3), Lewisite (L), nerve gases that include phosphonofluoridates such as Tabun (GA), Sarin (GB) and Soman (GD) and V compounds that include phosphorylthiocholines such as VX. Vesicants act as blistering agents that attack skin and mucous membranes. Nerve agents act on the central nervous system by reacting with the enzyme acetylcholinesterase to cause respiratory collapse, convulsions and death.

Methods for decontamination of chemical warfare agents, which include a variety of organophosphorus and organosulfur compounds, are known in the art. However, these known methods use compositions which have certain undesirable properties, including corrosiveness, flammability and toxicity. For example, hypochlorite formulations are very corrosive and toxic. Additionally, application of the hypochlorite decontaminant often requires substantial scrubbing for removal and destruction of the chemical warfare agent, a procedure which limits its use.

One decontaminant, Decontamination Solution 2 (DS2) used by the United States Army, is useful against a variety of chemical and biological warfare agents. DS2 contains 70% diethylenetriamine, 28% ethylene glycol monomethyl ether and 2% sodium hydroxide. However, DS2 spontaneously ignites upon contact with hypochlorites and hypochlorite-based decontaminants. Further, DS2 may cause corrosion to aluminum, cadmium, tin and zinc after prolonged contact, and softens and removes paint. Similar corrosion and human toxicity problems exist with the bleach decontamination solution (HTH) used by the United States Navy. Current decontamination solutions, while effective against both chemical and biological agents, use hydrogen peroxide as the primary oxidant. Liquid hydrogen peroxide presents handling, storage, and shipping problems. These solutions, in the mixed form, tend to offgas and foam.

Strong oxidizers may be used to detoxify warfare agent, however, several problems exist with the use of the strong oxidizers. The reactivity of most strong oxidizers inhibit long shelf life of any decontaminating solution, tend to be corrosive, and are hazardous to humans and the environment. Also, most of the strong oxidizers are liquids, making shipping and storage a problem.

In view of the foregoing, there is a need for an effective chemical and biological warfare agent decontamination solution that is particularly effective against hazardous biological organisms while being non-corrosive, nontoxic, nonflammable, and environmentally safe. The present invention addresses this and other needs.

SUMMARY OF THE INVENTION

The present invention includes a microemulsion composition for decontaminating chemical and biological warfare agent comprising a microemulsion, a solid source of peroxycarboxylic acid dissolved in the microemulsion and a germinant in combination with the solid peroxycarboxylic acid within the microemulsion. The present invention also includes a chemical and biological warfare decontamination composition, and a kit, having this microemulsion composition. Additionally, the present invention includes an area decontamination system comprising the microemulsion composition.

Furthermore, the present invention includes a process for decontaminating a contaminated surface comprising the steps of providing the microemulsion composition and applying the microemulsion composition to the contaminated surface in a manner that is effective for decontamination of the contaminated surface. A decontaminated surface product produced by this process is part of the present invention.

DETAILED DESCRIPTION OF THE PREFERRED EMBODIMENT

The present invention combines a solid, stable oxidant and a spore germinant into a microemulsion formulation to produce a decontaminating solution. Advantageously, this combination provides a superior composition to neutralize the threat chemical agents, such as VX, HD, and GD, while providing an effective disinfectant against biological agents, such as vegetative bacterial cells and spores, fungi, viruses and the like. As such, the present invention provides a novel microemulsion composition useful in decontamination of chemical and biological warfare agents.

The microemulsion composition of the present invention uses a solid source of peroxycarboxylic acid dissolved in the microemulsion in combination with the germinant. With the component parts of the decontaminating solution mixed, the peroxycarboxylic acid is available for degradation of the chemical and biological warfare agents. The peroxycarboxylic acid, an oxidizing agent, attacks the chemical and biological warfare agents. As the peroxycarboxylic acid attacks the warfare agent, the microemulsion provides a medium to enhance contact of the peroxycarboxylic acid with the chemical warfare agents. Once the warfare agent has been detoxified, the residual components of the decontaminating solution and warfare agent may be removed by any known method, such as a water rinse, or soap and water. Any known method of rinsing may be used, such as application of the water by hose, mop, scrubbers and the like.

The microemulsion of the present invention includes any appropriate system for suspension or dissolution of the solid source of peroxycarboxylic acid and germinant combination. The microemulsion preferably includes a surfactant composition or system having one or more surfactants, water and hydrocarbon compound. Low interfacial tension of the surface active compounds found within the emulsion helps dissolve the warfare agents, aiding detoxification from increased intimate contact between the oxidizer and warfare agent. The microemulsion preferably comprises the combined surfactant component in an amount of from about 5 wt % to about 60 wt %, water in an amount of from about 5 wt % to about 60 wt %, and hydrocarbon compound in an amount of from about 5 wt % to about 60 wt %. An exemplary microemulsion composition includes approximately 42.4 wt % water, 17.2 wt % decane and 24.6 wt % surfactants (neat). Buffers, and other known microemulsion additives may be added, as desired. Microemulsions have been disclosed to extract warfare agents which are then washed off, as detailed in U.S. Pat. No. 5,612,300 to von Blucher et al., the disclosure of which is herein incorporated by reference.

Preferred microemulsion systems include surfactants, particularly surfactants such as didecyl methylamine oxide, dimethyl decylamine oxide, and combinations thereof. Surfactants used within the microemulsion preferably include two amine oxide surfactants. The amine oxide surfactants may include, for example, any N-alkyldimethylamine or N-dialkylmethylamine oxide, having $C_{10}$, $C_{12}$, $C_{14}$, $C_{16}$ alkyls or mixtures of these. Exemplary surfactants include didecyl methylamine oxide manufactured by Albemarle Chemical of Baton Rouge, La. and sold under the tradename "Damox 1010" (76%), and decyl dimethylamine oxide manufactured by Lonza Chemical of Fair Lawn, N.J., and sold under the tradename "Barlox 10S" (30%). Preferred surfactant systems include amine oxides.

Preferably, microemulsions of the present invention comprise a water content of from about 20% to about 50% by weight with a hydrocarbon component dispersed therein. The hydrocarbon or oil component of the microemulsion may non-exclusively include alkane compounds with from about $C_5$ or higher, such as decane ($C_{10}$), dodecane ($C_{12}$), tetradecane ($C_{14}$), and hexadecane ($C_{16}$). The alkane should be nontoxic, nonflammable and resistant to oxidation. The hydrocarbon component is preferably present in amounts of from about 10% to about 30% by weight.

The peroxycarboxylic acids, also known as peracids, of the present invention provide a strong oxidizer that is effective in decontamination solutions to detoxify nerve agent, such as VX and HD with the G-agents readily neutralized at a moderately elevated pH. The peroxycarboxylic acid oxidizers of the present invention include peracetic acid (PAA) for effectiveness against chemical agents while possessing a high decontaminant activity against bacteria, fungi, and viruses. Representative peracids of the present invention are described in U.S. Pat. No. 6,369,288, to Brown, entitled "Chemical and Biological Warfare Decontaminating Solution Using Bleach Activators", the disclosure of which is herein incorporated by reference for the teaching of peroxycarboxylic acids. The preferred peracetic acid source is peracetyl borate (PAB). Peracids are strong oxidizers that leave a limited environmental footprint because of their breakdown products of water and a weak acid. At a moderate pH range, the peracids are effective and non-corrosive to machinery and other articles, such as military materials.

Synthesis of peracetyl borate is described by Roesler, et al. in U.S. Pat. No. 5,462,692, to Roesler et al., entitled "Stable Solid Acetyperoxyborate Compounds", the disclosure of which is hereby incorporated by reference for such teachings. Use of the peracid as a decontaminant in a chemical/biological decontamination formulation substantially destroys or eliminates all forms of microbial life in the inanimate environment, including forms of vegetative bacteria, fingi, and viruses.

Effective amounts of the peroxycarboxylic acid are determinable by those skilled in the art for specific concentrations of warfare agent, types and amounts of germinant, contact methods, additional chemical warfare countermeasures, operational necessities, and other like factors considered for personnel ingress and egress from an exposed area. Preferably, effective detoxification includes normal human contact within a previously contaminated environment that has been treated with the decontamination solution of the present invention without any adverse health effects. Preferred amounts includes, for example without limitation, from about 0.01 g/mL to about 0.20 g/mL, with a more preferred amount in the range of from about 0.03 g/mL to about 0.15 g/mL, and with a most preferred amount in the range of from about 0.04 g/mL to about 0.10 g/mL.

Of the three broad classes of biological threats (bacteria, fungi, and viruses), the endospore forming bacteria presents the most difficult threat to neutralize. Spores have a highly protective coat and can remain dormant for extended periods of time. Under certain conditions, such as temperature, moisture, and/or chemical stimulus, spores germinate and become vegetative cells. In this vegetative state the endospore forming bacteria are most vulnerable to decontamination. The decontamination solution of the present invention contains three elements effective biological decontamination. These three elements include a strong oxidizer, surfactants to reduce the surface tension between the spores and the components of the decontamination solution, and a germinant to induce germination.

The present invention includes a type and amount of germinant that is effective to germinate resident spores within the contamination. This germination allows for a broad, more complete, decontamination of the hazard. Germinants of the present invention include, for example without limitation, dipicolinic acid, alanine, asparagine, glucose, fructose, potassium chloride, and the like, and combinations thereof. The preferred germinant of the present invention includes dipicolinic acid (DPA), that more preferably includes the presence of calcium ions. Representative amounts of germinant include from about 0.03 molar amount to about 0.30 molar amount, with a more preferred range of from about 0.15 molar amount to about 0.25 molar amount. The pH of the microemulsion composition preferably ranges from about 7 to about 10, such as from about 8 to about 9.5.

A preferred microemulsion composition for decontaminating chemical and biological warfare agent includes a surfactant of didecyl methylamine oxide and dimethyl decylamine oxide, peracetyl borate and dipicolonic acid. This formulation, and other formulations taught herein, may be incorporated into a kit or an area decontamination system.

Within the microemulsion, the mixed peracid and germinant remain stable with no offgassing or foaming generally occurring. Additionally, the microemulsion provides a compatibility, e.g., non-corrosive properties, with military materials, and is generally safe for the user and immediate environment of use.

In operation, the decontaminating solution of the present invention is applied onto a contaminated area or surface to neutralize or detoxify the chemical and/or biological warfare agent. Application of the decontamination solution includes placing the peracid in a microemulsion, and incorporating a germinant together with the peracid. The combination of the peracid and germinant in the microemulsion system or composition provides a synergistic effect in killing spores while the peroxycarboxylic acid neutralizes chemical agents. The microemulsion composition is contacted with a biological and/or chemical warfare agent that reacts with the peroxycarboxylic acid and become detoxified. Representative applications of the microemulsion include, for example without limitation, application by mops, brushes, sprayers and other known solution applicators. The decontaminating solution of the present invention is noncorrosive, nontoxic, and nonflammable, and useful in rapidly neutralizing individual and combinations of chemical and biological warfare agents, such as VX, GD and HD, and vegetative and endospore forming bacteria, fungi and virus. The resultant decontaminated surface is free of contamination.

EXAMPLE 1

3,023 mg of an alkane sulfonate surfactant blend of approximately 52% of Clariant's Hostapur SAS-30 (secondary alkane sulfonate, sodium salt) and 48% of Dow Chemical's Dowfax Hydrotrope (benzene 1,1'-oxybis-,sec-hexyl derivative, sulfonated sodium salts) was weighed into a reaction vessel. 1,483 μL of 3.0 M KOH solution was added and mixed. Chemical agent sufficient to achieve a concentration of 0.1 M was added and mixed. 660 μL of 15% peracetic acid solution was added and mixed. A 15-minute decontamination period was allowed followed by neutralization and determination of the amount remaining chemical agent.

The peracetic acid used in Example 1 was a commercial solution of 15% peracetic acid. The disadvantage of the peracetic acid solution is stability evidenced by foaming and offgassing in the mixed system. As the commercial grades of PAA are mixtures of acetic acid, hydrogen peroxide, peracetic acid, stabilizing agents, and water, the foaming and offgassing is caused by the hydrogen peroxide.

The results of Example 1 are shown in Table 1, below.

TABLE 1

CHEMICAL AGENT EFFICIENCY
Decon Efficiency of 0.1 M Chemical Agent by 0.3 M PAA, Mixed Sulfonate μEm, Buffered to pH = 10

| | % Agent Neutralized | | |
|---|---|---|---|
| Reaction Time, min | HD | GD | VX |
| 0 | 0.00 | 0.00 | 0.00 |
| 15 | 98.21 | 99.99 | 98.39 |
| 30 | 98.31 | 99.99 | 98.58 |
| 60 | 99.15 | 99.99 | 98.72 |

EXAMPLE 2

342 mg of a mixed amine oxide surfactant blend of approximately 14% of Albemarle's Damox 1010 and 86% of Lonza's Barlox 10S, 646 mg of deionized water, 75 mg of sodium Carbonate, and 10 mg of dipicolinic acid were weighed into a vial and mixed until homogeneous. 125 mg of peracetyl borate was added to a second vial. The contents of the two vials were combined and mixed until the solid peracetyl borate is fully dissolved. The solution was transferred to a 5 mm Nuclear Magnetic Resonance (NMR) tube. Chemical agent sufficient to achieve a concentration of 0.1 M was added to the NMR tube. The reaction progress was monitored by NMR spectroscopy.

The stability problems found in Example 1 were resolved by the use of a solid form of peracetic acid called peracetyl borate. Upon dissolution in water, peracetyl borate generates peracetic acid with minimal generation of hydrogen peroxide. Decontamination systems incorporating the peracetyl borate retain the advantage of having a strong oxidizer such as peracetic acid, without the foaming and offgassing observed with formulations containing hydrogen peroxide.

Incorporation of peracetyl borate into a microemulsion yielded a very stable formulation with no offgassing or foaming. The high decontamination efficiency of the peracetyl borate microemulsion formulation toward the chemical agents is shown in Table 2, below.

TABLE 2

CHEMICAL AGENT EFFICIENCY
Decon Efficiency of 0.1 M CA by 0.3 M PAB, Mixed Amine Oxide Surfactant μEm, Buffered to pH = 8.5

| | % Agent Neutralized | | |
|---|---|---|---|
| Reaction Time, min | HD | GD | VX |
| 0 | 0.0 | 0.0 | 0.0 |
| 15 | 100.0 | 97.2 | 56.6 |

EXAMPLE 3

The effectiveness of various combinations of microemulsion, peracid and germinant were tested.

For formulation A, 135 mg of didecyl methylamine oxide was brought to a volume of 4 mL with deionized water. For formulation B, 1178 mg of dimethyl decylamine oxide was brought to a volume of 4 mL with deionized water. For formulation C, 1368 mg of a mixed amine oxide surfactant blend of approximately 14% of Albemarle's Damox 1010 and 86% of Lonza's Barlox 10S, 2584 mg of deionized water, and 300 mg of sodium carbonate were weighed into a vial and mixed until homogeneous. 500 mg of peracetyl borate was added to a second vial. The contents of the two vials were combined and mixed until the solid peracetyl borate was fully dissolved. For formulation D, 40 mg of dipicolinic acid was brought to a volume of 4 mL with deionized water. For formulation E, 528 μL of 15% commercial peracetic acid solution was brought to a volume of 4 mL with deionized water.

10 μL of a suspension of *Bacillus globigii* spores with a concentration of $10^{10}$ colony forming units (CFU) were added to a reaction vessel. 990 μL of the formulation were added to a reaction vessel. The reaction mixture was stirred for 15 minutes. In formulations C and E, the reaction mixture was neutralized with 1 mL of sodium metabisulfite solution with a concentration of 330 mg/mL. The remaining *Bacillus globigii* spores were isolated and serial dilutions were performed. The dilutions were plated on LB agar. Colonies were counted following incubation of the plates for 24 hours at 37 degrees C.

Formulations A and B contained $10^8$ *Bacillus globigii* spores and the individual surfactants of the amine oxide microemulsion in concentrations used in the microemulsion system. Formulation C contained $10^8$ *Bacillus globigii* spores and 0.38 M peracetyl borate in the mixed amine oxide (2.3% didecyl methylamine oxide and 8.8% dimethyl decylamine oxide) microemulsion system of 4 mL. Formulation D contained $10^6$ *Bacillus globigii* spores and 0.1 M dipicolinic acid. Formulation E contained $10^8$ *Bacillus globigii* spores and 264 μL of 15% commercial peracetic acid solution (containing 600 ppm dipicolinic acid as a stabilizer).

TABLE 3

BIOCIDAL EFFICIENCY
Reduction in *Bacillus globigii* After Exposure to Candidate Solutions

| | Initial CFU/mL | Log Reduction, CFU/mL |
|---|---|---|
| A: Didecyl methylamine oxide surfactant | $10^8$ | 0 in 30 minutes |
| B: Dimethyl decylamine oxide surfactant | $10^8$ | 0 in 30 minutes |
| C: PAB in mixed amine oxide μEm | $10^8$ | 4 in 15 minutes |
| D: DPA | $10^6$ | 0 in 15 minutes |
| E: PAA | $10^8$ | 4 in 15 minutes |

Note: Due to the reactive nature of the systems for Formulations C and E, a neutralization step was needed. The neutralization step included the addition of 1 mL of 330 mg/ml sodium metabisulfite solution.

Example 3 demonstrated the ineffectiveness of the amine oxide surfactants individually (Formulations A & B), the surfactants combined with peracetyl borate (Formulation C), the dipicolinic acid alone (Formulation D), or a combination of oxidizers and dipicolinic acid (Formulation E).

EXAMPLE 4

A series of experiments was conducted on the effectiveness of formulations containing microemulsion compositions containing a peracid and germinant. Formulation F contains *Bacillus globigii* spores, surfactants and a 15% commercial peracetic acid solution. Formulation G contains *Bacillus globigii* spores, surfactants, peracetyl borate and dipicolinic acid.

1368 mg of a mixed amine oxide surfactant blend of approximately 14% of Albemarle's Damox 1010 and 86% of Lonza's Barlox 10S, 2584 mg of deionized water, 300 mg of sodium carbonate, and 40 mg of dipicolinic acid were weighed into a vial and mixed until homogeneous. 500 mg of peracetyl borate was added to a second vial. The contents of the two vials were combined and mixed until the solid peracetyl borate was fully dissolved. 10 μL of a suspension of *Bacillus globigii* spores with a concentration of $10^{10}$ colony forming units was added to a reaction vessel. 990 μL of the decontamination solution was added to the reaction vessel. The reaction mixture was stirred for 15 minutes. The reaction mixture was neutralized with 1 mL of sodium metabisulfite solution with a concentration of 330 mg/mL. The remaining *Bacillus globigii* spores were isolated and serial dilutions were performed. The dilutions were plated on LB agar. Colonies were counted following incubation of the plates for 24 hours at 37 degrees C.

TABLE 4

BIOCIDAL EFFICIENCY
Reduction in *Bacillus globigii* from $10^8$ Initial CFU/mL
After 15 Minute Exposure to Candidate Solutions

| | Log Reduction, CFU/mL |
|---|---|
| F: PAA in mixed amine oxide μEm | 8 |
| G: PAB and DPA in mixed amine oxide μEm | 8 |

The series of experiments are summarized in Table 5, below.

TABLE 5

SUMMARY PEROXYGEN BIOCIDAL EFFICIENCY TESTS

| Formulation | Surfactant | Oxidizer | Germinant | Effectiveness* |
|---|---|---|---|---|
| Formulation A | Yes | No | No | No |
| Formulation B | Yes | No | No | No |
| Formulation C | Yes | Yes | No | No |
| Formulation D | No | No | Yes | No |
| Formulation E | No | Yes | Yes | No |
| Formulation F | Yes | Yes | Yes | Yes |
| Formulation G | Yes | Yes | Yes | Yes |

*Effectiveness against *Bacillus globigii* spores.

Live agent tests with *Bacillus anthracis* (anthrax) confirmed these results. 1368 mg of a mixed amine oxide surfactant blend of approximately 14% of Albemarle's Damox 1010 and 86% of Lonza's Barlox 10S, 2584 mg of deionized water, 300 mg of sodium carbonate, and 40 mg of dipicolinic acid were weighed into a vial and mixed until homogeneous. 500 mg of peracetyl borate was added to a second vial. The contents of the two vials were combined and mixed until the solid peracetyl borate was fully dissolved. 100 μL of a suspension of *Bacillus anthracis* spores with a concentration of $10^8$ colony forming units was added to a reaction vessel. 900 μL of the decontamination solution was added to the reaction vessel. The reaction mixture was stirred for 15 minutes. The reaction mixture was neutralized with 1 mL of sodium metabisulfite solution with a concentration of 330 mg/mL. The remaining anthrax spores were isolated and serial dilutions were performed. The dilutions were plated on 5% sheep's blood agar. Colonies were counted following incubation of the plates for 48 hours at 37 degrees C.

In Formulation H, peracetyl borate with dipicolinic acid in a mixed amine oxide surfactant system demonstrated excellent decontamination ability with *Bacillus anthracis*, as shown in Table 6, below.

TABLE 6

| BIOCIDAL EFFICIENCY Reduction in *Bacillus anthracis* from $10^7$ Initial CFU/mL, 15 Minute Exposure to Candidate Solutions | Log Reduction, CFU/mL |
|---|---|
| H: PAB and DPA in mixed amine oxide μEm | 7 |

The present invention provides decontamination technology that is superior to combinations of surfactants (macro or microemulsions) in decontamination solutions, peracids in a decontamination solution, peracids as a biocide, or the application of a germinant formulation prior to or concurrent with application of decontamination solution. Uniquely, the present invention may use a solid peracetyl borate as a means of producing a stable, non-foaming chemical/biological decontamination solution. Additionally, the present invention includes an oxidizer, surfactant(s) and germinant, in a combination chemical and biological decontamination formulation. This allow the surfactants to bring the reactants in contact with the agents and spores, causing the spores to germinate with a non-metabolizable compound and reducing the concentration of chemical and biological agents with the peracetic acid from the solid peracetyl borate.

The present invention provides several advantages. These include the ability to significantly reduce or neutralize, within a reasonable amount of time, the effects of chemical agents using peracetyl borate as the oxidizer in a microemulsion system, shown in testing of VX, HD, and GD with the ability to neutralize, within a reasonable amount of time, the effects of biological warfare agents using a combination of surfactants, oxidizer, and germinant, shown in testing of the anthrax simulant *Bacillus globigii* as well as *Bacillus anthracis*. The present invention allows storage of oxidative components of the decontamination system for periods of time greater than several months with the ability to safely and easily handle and store the oxidative components of the decontamination system. The reaction products of the reactive components of the decontamination solution are water and weak acids which lowers toxicity to humans and produces smaller environmental footprint.

Specifically, the microemulsion allows for intimate contact of the chemical/biological agents with germinant(s) and peracid(s), and the stability of the peracid source allows for easy handling and storage of the decontamination solution components. The decontaminating agent compositions of the present invention are nontoxic and useful in detoxifying/neutralizing a variety of chemical warfare agents, including organosulfur agents such as mustard gas, and organophosphorus agents such as the nerve agents termed VX and GD. The decontaminating agents of the present invention may also be used to neutralize selected organophosphorus agricultural chemicals. Decontamination is effected by applying a decontaminating agent of the present invention to the contaminated material, equipment, personnel, or the like. Such application includes any suitable means for applying a solution onto a contaminated surface, with the type and manner of application determinable by those skilled in the art, such as spraying, showering, washing or other suitable means. Generally, such application is guided by decreasing the exposure, initial or continuous, of the contaminating warfare agent to personnel with the amount of decontaminating solution required under military operational conditions can be readily determined by those skilled in the art.

The foregoing summary, description, and examples of the present invention are not intended to be limiting, but are only exemplary of the inventive features that are defined in the claims.

What is claimed is:

1. A process for decontaminating a surface contaminated by a chemical warfare agent, comprising:

providing a microemulsion composition having a microemulsion, peracetyl borate as a solid source of peroxycarboxylic acid dissolved in the microemulsion and a germinant in combination with the peracetyl borate within the microemulsion; and applying the microemulsion composition to the contaminated surface effective for decontamination of the chemical warfare agent thereof.

2. The process of claim 1, wherein the germinant comprises dipicolinic acid.

3. The process of claim 1, wherein the microemulsion composition comprises a surfactant selected from the group consisting of didecyl methylamine oxide, dimethyl decylamine oxide, and combinations thereof.

4. The process of claim 1, wherein the peroxycarboxylic acid is present in an amount of from about 0.03 g/mL to about 0.20 g/mL.

5. The process of claim 4, wherein the peroxycarboxylic add is present in an amount of from about 0.10 g/mL to about 0.15 g/mL.

6. The process of claim 1, wherein the germinant is selected from the group consisting of dipicolinic acid, alanine, asparagine, glucose, fructose, potassium chloride, and combinations thereof.

7. The process of claim 6, wherein the germinant comprises dipicolinic acid.

8. The process of claim 7, wherein the dipicolinic acid is present in an amount of from about 0.03 molar amount to about 0.30 molar amount.

9. The process of claim 8, wherein the dipicolinic acid is present in an amount of from about 0.15 molar amount to abdut 0.25 molar amount.

10. The process of claim 1, further comprising a pH of the composition ranging from about 7.0 to about 10.0.

11. The process of claim 1, wherein the microemulsion is selected from the group consisting of didecyl methylamine oxide, dimethyl decylamine oxide, and combinations thereof; and the germinant comprises dipicolonic acid effective for spore germination in combination with the peracetyl borate within the microemulsion.

* * * * *